(12) United States Patent
Schadt et al.

(10) Patent No.: US 8,523,986 B2
(45) Date of Patent: Sep. 3, 2013

(54) GAS SCRUBBER AND USE OF THE GAS SCRUBBER

(75) Inventors: Arne Schadt, Linz (AT); Juergen Eberhardt, Rodgau (DE); Martin Mueller-Hasky, Heusenstamm (DE)

(73) Assignee: Lurgi GmbH, Frankfurt Am Main (DE)

( * ) Notice: Subject to any disclaimer, the term of this patent is extended or adjusted under 35 U.S.C. 154(b) by 897 days.

(21) Appl. No.: 12/527,243

(22) PCT Filed: Feb. 12, 2008

(86) PCT No.: PCT/EP2008/001047
§ 371 (c)(1),
(2), (4) Date: Jan. 21, 2010

(87) PCT Pub. No.: WO2008/098732
PCT Pub. Date: Aug. 21, 2008

(65) Prior Publication Data
US 2010/0137589 A1      Jun. 3, 2010

(30) Foreign Application Priority Data
Feb. 16, 2007 (DE) .......................... 10 2007 007 746

(51) Int. Cl.
*B01D 47/00* (2006.01)
(52) U.S. Cl.
USPC ................. 96/243; 95/149; 95/228; 261/116; 261/142
(58) Field of Classification Search
CPC ....................................................... B01F 3/04
USPC ........................ 261/116, 142; 95/149, 228
See application file for complete search history.

(56) References Cited

U.S. PATENT DOCUMENTS

| | | | |
|---|---|---|---|
| 1,964,357 A | 6/1934 | Ketterer | |
| 3,700,672 A | 10/1972 | Kokubo et al. | |
| 3,746,322 A | 7/1973 | Sawyer | |
| 5,336,284 A * | 8/1994 | Schifftner | 96/323 |
| 5,707,426 A * | 1/1998 | Kalka et al. | 95/200 |
| 2009/0030201 A1 * | 1/2009 | Muller-Hasky et al. | 544/201 |

FOREIGN PATENT DOCUMENTS

| | | | |
|---|---|---|---|
| DE | 1542406 A1 * | 4/1770 | |
| DE | 1542406 A1 | 4/1970 | |
| DE | 10229101 A1 | 7/2003 | |
| DE | 10 2005 023041 A1 | 11/2006 | |
| DE | 102005023041 A1 * | 11/2006 | |
| WO | 02/100840 A | 12/2002 | |

OTHER PUBLICATIONS

International Preliminary Report on Patentability, PCT/EP2008/001047 (Sep. 8, 2009).*
English Language Abstract for DE 10 2005 023041, Jul. 29, 2009.
English Language Abstract for DE 15 42 406, Apr. 2, 1970.
English Language Abstract for DE 102 29 101, Jul. 17, 2003.

* cited by examiner

*Primary Examiner* — Robert A Hopkins
(74) *Attorney, Agent, or Firm* — Norris McLaughlin & Marcus PA

(57) ABSTRACT

In a gas scrubber, a gas stream containing at least one sublimed substance is brought in contact with a liquid or melt stream containing at least one thermally convertible substance, which has a lower temperature than the gas stream. For the intensive and intimate mixing of the gas stream with the liquid or melt stream, an orifice plate with a plurality of holes each surrounded by a retaining edge is provided in the upper part of the gas scrubber, and above the orifice plate inlets for the gas stream and the liquid or melt stream are provided.

4 Claims, 2 Drawing Sheets

GAS SCRUBBER AND USE OF THE GAS SCRUBBER

Figure 1:
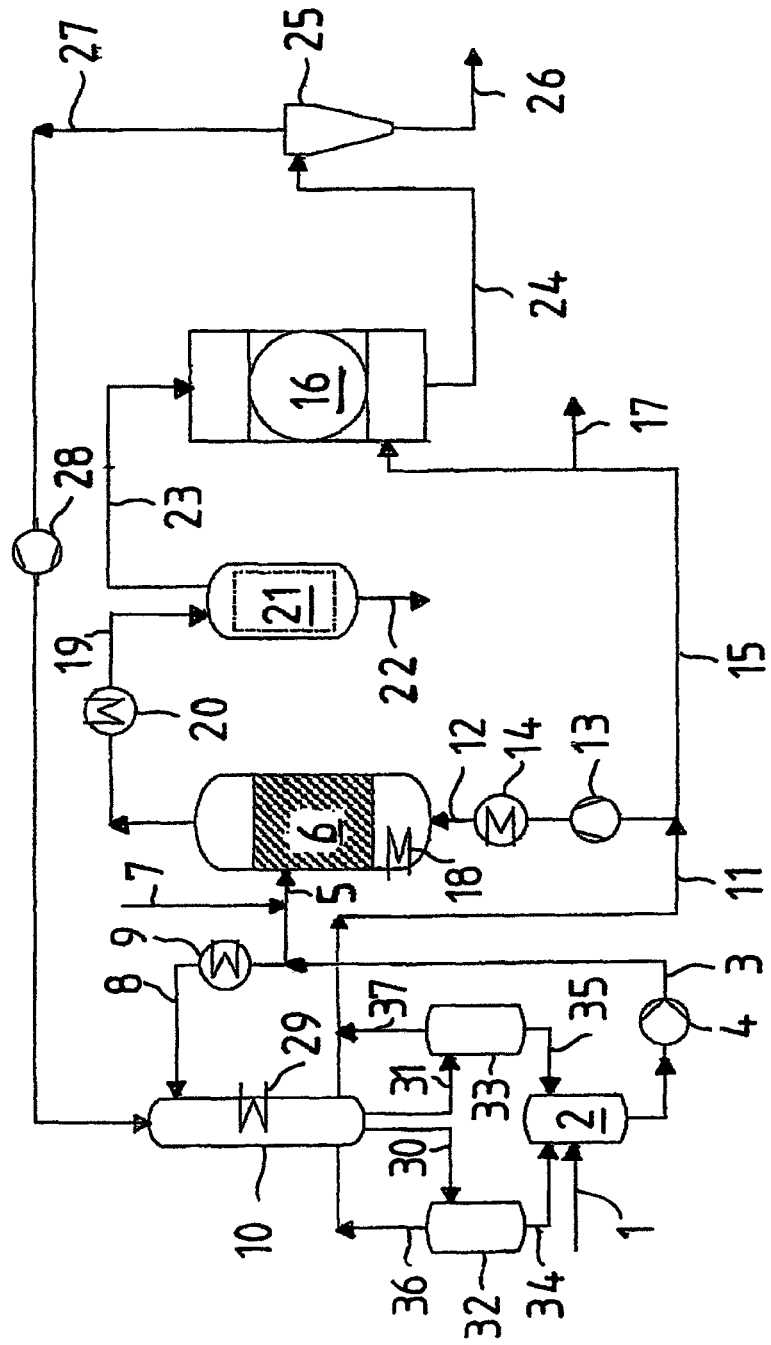

This application is a 371 application of PCT/EP2008/001047 filed Feb. 12, 2008, which claims priority to the German application DE 10 2007 007 746.9 filed Feb. 16, 2007.

This invention relates to a gas scrubber, in which a gas stream containing at least one sublimed substance is brought in contact with a liquid or melt stream containing a thermally convertible substance, which has a lower temperature than the gas stream, the use of the gas scrubber in an apparatus for producing $C_3N_3(NH_2)_3$ from $CO(NH_2)_2$, and a process for operating the apparatus for producing $C_3N_3(NH_2)_3$ from $CO(NH_2)_2$.

$C_3N_3(NH_2)_3$ is an important intermediate product obtained by trimerization of $CO(NH_2)_2$ for the production of thermosetting plastics, glues, adhesives etc. In conjunction with inorganic and organic acids, the salts of $C_3N_3(NH_2)_3$ have gained importance as flame retardants and as accelerators for aminoplastic resins. Proceeding from $CO(NH_2)_2$, $C_3N_3(NH_2)_3$ can be produced both by the high-pressure process in the presence of a commercially available catalyst, such as alumosilicates, alumina or silica gel, at a pressure of at least 80 bar[a] and by the low-pressure process in the presence of one of the aforementioned catalysts at a pressure of not more than 10 bar[a] and at a temperature of 380 to 410° C. in a fluidized bed according to the reaction equation

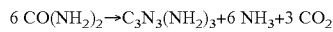

$$6\ CO(NH_2)_2 \rightarrow C_3N_3(NH_2)_3 + 6\ NH_3 + 3\ CO_2$$

wherein $NH_3$ or a mixture of $CO_2$ and $NH_3$ is used as fluidizing gas. Since the reaction proceeds endothermally, major amounts of heat must be supplied to the process from outside. Based on the amount of $CO(NH_2)_2$ used, the yield of $C_3N_3(NH_2)_3$ generally is 90 to 95%.

WO-A-2006/119815 describes a single-stage process for producing $C_3N_3(NH_2)_3$, in which molten $CO(NH_2)_2$ is reacted in a fluidized bed at a temperature of 395 to 400° C. and almost atmospheric pressure in the presence of a catalyst to obtain synthesis gas containing sublimed $C_3N_3(NH_2)_3$, $NH_3$ and $CO_2$ and traces of by-products, such as the polycyclic compounds melam and melem. Subsequently, the synthesis gas is cooled, then filtered to remove the by-products and the catalyst particles and thereafter supplied to a crystallizer, in which the synthesis gas is cooled to a temperature of 190 to 210° C. By cooling the synthesis gas, the sublimed $C_3N_3(NH_2)_3$ is resublimied for approximately 98%, and the $C_3N_3(NH_2)_3$ crystals formed are separated from the synthesis gas in a downstream separator and discharged from the process. The residual synthesis gas substantially containing $CO_2$, $NH_3$, HNCO and a small amount of sublimed $C_3N_3(NH_2)_3$ is charged to the head of a gas scrubber and cooled therein to a temperature of 190 to 220° C. with $CO(NH_2)_2$ melt having a temperature of 130 to 145° C., which is sprayed into the gas scrubber, so that the $C_3N_3(NH_2)_3$ contained in the residual synthesis gas is resublimed and HNCO is converted to $CO(NH_2)_2$ in the presence of $NH_3$. The resublimed $C_3N_3(NH_2)_3$, the washed gases $NH_3$ and $CO_2$ and the $CO(NH_2)_2$ are separately discharged from the gas scrubber and the $CO(NH_2)_2$ melt is recirculated into the process. One disadvantage of this process consists in that in the upper part of the gas scrubber resublimed $C_3N_3(NH_2)_3$ is precipitated on the internal fittings due to the relatively poor mixing of $CO(NH_2)_2$ and $C_3N_3(NH_2)_3$ resublimed in the residual synthesis gas and can be removed therefrom only by using mechanical aids. In addition, there is a tendency that reaction products of urea, such as cyanuric acid, biuret, triuret etc., are deposited on hardly accessible points of the gas scrubber.

It is the object of the present invention to provide a gas scrubber, in which a gas stream containing at least one sublimed substance can intimately be mixed with a liquid or melt stream containing at least one thermally convertible substance, which has a lower temperature than the gas stream, already at the beginning of the contact between the two streams.

This object is solved by at least one orifice plate arranged in the upper part of the gas scrubber, comprising a plurality of holes each surrounded by a retaining edge, inlets for the gas stream and the liquid or melt stream, which are arranged above the orifice plate, a heat exchanger arranged below the orifice plate in the contact path in which the gas stream gets in contact with the liquid or melt stream, and outlets for the cleaned gases and the liquid or melt stream, which are arranged separately in the lower part of the gas scrubber.

The liquid or melt stream and the gas stream directed onto the orifice plate via corresponding inlets initially are prevented from directly flowing off via the holes of the orifice plate by the retaining edges surrounding the holes. Due to the congestion formed, the liquid or melt stream and the gas stream start to mix. The mixing effect is improved in that the inlets for the liquid or melt stream and the gas stream are arranged in the gas scrubber in opposite directions. As soon as the mixture exceeds the apex of the retaining edges, the mixture flowing down over the retaining edges and the holes generates a negative pressure and the flow rate is increased with the consequence that an increased contact between gas and liquid or melt takes place.

A very intensive and intimate contact between gas and liquid or melt then is achieved when according to a particular feature of the invention the retaining edge surrounding the holes has the shape of a cone or of the upper portion of a rotation paraboloid and on the bottom surface of the orifice plate there is each provided an edge surrounding the holes in the form of a counter-cone or counter-portion of the rotation paraboloid. Due to the two cones or portions of the rotation paraboloid directed against each other, which are joined at the smallest cross-section, i.e. in the holes of the orifice plate, a greater negative pressure and an increase of the flow rate of the mixture formed of gas and liquid or melt is achieved at the narrowest point. At the narrowest point, the dynamic pressure is at a maximum and the static pressure is at a minimum. The flow rate of the mixture rises when traversing the inlet cone or the inlet portion of the rotation paraboloid, and at the same time the pressure in the outlet cone or in the outlet portion of the rotation paraboloid is decreasing. Due to the resulting flow conditions, a homogeneous mixture of gas and liquid or melt is produced.

The gas scrubber designed in accordance with the invention is suitable in particular for use in an apparatus for producing $C_3N_3(NH_2)_3$ from $CO(NH_2)_2$. The apparatus consists of a fluidized-bed reactor for converting $CO(NH_2)_2$ in the presence of a commercially available catalyst at a temperature of 380 to 420° C. and a pressure of not more than 10 bar[a] to a synthesis gas containing sublimed $C_3N_3(NH_2)_3$ as well as $NH_3$, $CO_2$ and HNCO, a heat exchanger for cooling the synthesis gas to a temperature of 210 to 300° C., a gas filter for removing dust-like catalyst particles contained in the synthesis gas and by-products of the catalytic conversion, such as melem and melam, a crystallizer for resubliming the sublimed $C_3N_3(NH_2)_3$ by cooling the synthesis gas to a temperature of 180 to 210° C., a separator for removing the $C_3N_3(NH_2)_3$ crystals formed by resublimation from the synthesis gas, a gas scrubber for removing the gas components $CO_2$, NH$_3$, HNCO contained in the residual synthesis gas and possibly traces of sublimed C$_3$N$_3$(NH$_2$)$_3$ and separate outlets for the cleaned gas mixture containing NH$_3$ and CO$_2$ as well as the CO(NH$_2$)$_2$ melt from the gas scrubber. By the gas scrubber designed in accordance with the invention, the CO(NH$_2$)$_2$ melt introduced into the gas scrubber and the residual synthesis gas supplied are mixed with each other so intensively and intimately that neither sublimed C$_3$N$_3$(NH$_2$)$_3$ possibly present in traces in the residual synthesis gas nor reaction products of the CO(NH$_2$)$_2$ are precipitated on internal fittings of the gas scrubber or on inaccessible points of the gas scrubber. The CO(NH$_2$)$_2$ melt having a temperature of 120 to 150° C., preferably 135 to 145° C., and the residual synthesis gas having a temperature of 190 to 210° C. flow onto the orifice plate in streams directed against each other and mix on the orifice plate to obtain a heterogeneous mixture, which flows off with a mixing temperature of 155 to 175° C. through the holes of the orifice plate into the portion of the gas scrubber disposed thereunder by forming a homogeneous mixture of CO(NH$_2$)$_2$ melt and residual synthesis gas. On the contact path below the orifice plate, the homogeneous mixture is cooled to a temperature of 130 to 150° C.

Figure 2:
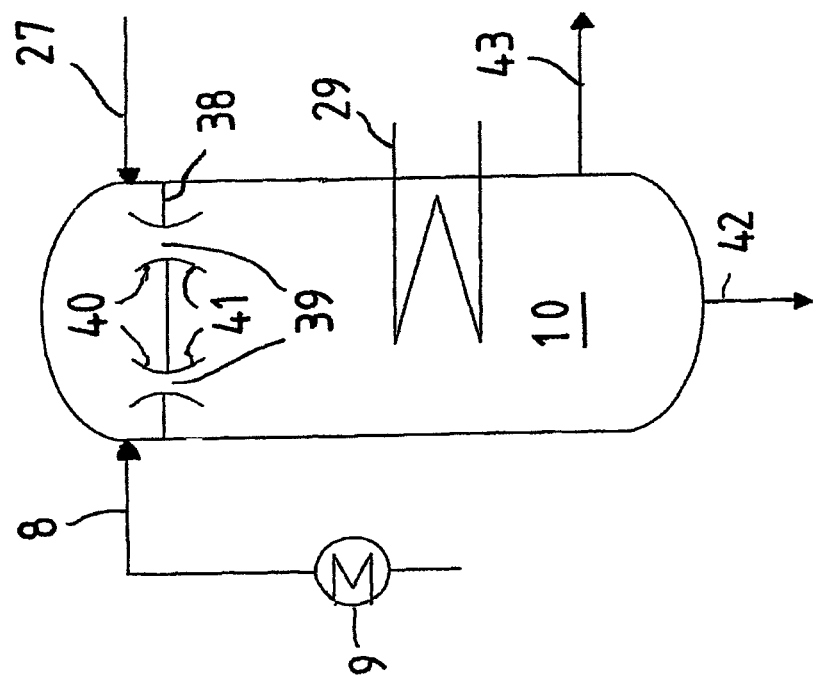

The invention will be explained in detail by an embodiment and a basic flow diagram represented in the drawing as well as by a schematic longitudinal section of a gas scrubber. In the drawing:

FIG. 1 shows a basic flow diagram of a low-pressure process for producing C$_3$N$_3$(NH$_2$)$_3$, and FIG. 2 shows a schematic longitudinal section through a gas scrubber for use in the apparatus for producing C$_3$N$_3$(NH$_2$)$_3$ as shown in FIG. 1.

As shown in FIG. 1, CO(NH$_2$)$_2$ melt with a temperature of 135 to 145° C. is withdrawn from the storage tank (2) filled with CO(NH$_2$)$_2$ melt via conduit (1) and is charged through conduit (3) via the pump (4) and for one part through conduit (5) to the fluidized-bed reactor (6), in which for instance Al$_2$O$_3$ is used as catalyst. Directly before entry of the CO(NH$_2$)$_2$ melt into the fluidized-bed reactor (6), NH$_3$ supplied through conduit (7) is fed into the CO(NH$_2$)$_2$ melt flowing in conduit (5), in order to achieve spraying of the CO(NH$_2$)$_2$ melt directly upon entry thereof into the fluidized-bed reactor (6) with the consequence of an immediate evaporation of the CO(NH$_2$)$_2$ melt. The other part of the CO(NH$_2$)$_2$ melt serving as washing agent circulates through conduit (8) over the heat exchanger (9), in which the melt is cooled to a temperature of 120 to 130° C., into the gas scrubber (10) via the inlet provided at the head. From the lower part of the gas scrubber (10), a gas mixture containing NH$_3$ and CO$_2$, which has a temperature of 120 to 150° C., is withdrawn via conduit (11) and for one part passed as fluidizing gas through conduit (12) over the compressor (13) and the heat exchanger (14) used for preheating to a temperature of 380 to 420° C. into the lower part of the fluidized-bed reactor (6) and for the other part charged as cooling gas through conduit (15) to the crystallizer (16). It is possible to withdraw the gas mixture of conduit (15), which contains NH$_2$ and CO, from the process through conduit (17). In the lower portion of the fluidized-bed reactor (6), a heat exchanger (18) is provided, with which heat required in addition for the catalytic conversion can be introduced into the fluidized bed. The temperature of the fluidized bed is 380 to 420° C. Together with the fluidizing gas and the NH$_3$ and CO$_2$ newly formed during the catalytic conversion, the C$_3$N$_3$(NH$_2$)$_3$ sublimed as a result of the catalytic conversion in the fluidized-bed reactor (6) flows through conduit (19) over the heat exchanger (20), in which the gas mixture is cooled to a temperature of 210 to 300° C., so that the by-products obtained during the catalytic conversion in the fluidized-bed reactor (6), such as melem and melam, are condensed. The by-products and the entrained dust-like catalyst particles contained in the gas mixture are separated in the downstream gas filter (21) and discharged from the process through conduit (22). Through conduit (23), the gas mixture cleaned of by-products of the catalytic conversion and entrained dust-like catalyst particles is introduced into the crystallizer (16), in which the gas mixture is cooled to a temperature of 150 to 250° C., preferably 190 to 210° C., by means of the gas mixture containing NH$_3$ and CO$_2$, which is supplied through conduit (15). Together with NH$_3$ and CO$_2$, the C$_3$N$_3$(NH$_2$)$_3$ resublimed in crystal form as a result of cooling is charged through conduit (24) to a separator (25), preferably a gas cyclone, in which the resublimed C$_3$N$_3$(NH$_2$)$_3$ crystals are deposited and discharged from the process through conduit (26). The residual synthesis gas, which contains NH$_3$, CO$_2$, HNCO and possibly traces of sublimed C$_3$N$_3$(NH$_2$)$_3$, is charged from the separator (25) through conduit (27) via the compressor (28) to the inlet mounted in the head of the gas scrubber (10). In the gas scrubber (10), the residual synthesis gas is washed with CO(NH$_2$)$_2$ melt having a temperature of 120 to 130° C. and at the same time cooled to a temperature of 130 to 150° C., by passing the CO(NH$_2$)$_2$ melt over a heat exchanger arranged in the middle portion of the gas scrubber (10). The CO(NH$_2$)$_2$ melt accumulates in the bottom of the gas scrubber (10) and is each supplied via conduits (30, 31) to a droplet separator (32, 33), in which the CO(NH$_2$)$_2$ melt and the deposited gas mixture containing NH$_3$ and CO$_2$ are separated from each other. The CO(NH$_2$)$_2$ melt is discharged from the droplet separators (32, 33) through conduits (34, 35) into the storage tank (2) for the CO(NH$_2$)$_2$ melt. The gas mixture containing NH$_3$ and CO$_2$, which is separated in the droplet separators (32, 33), is fed through conduits (36, 37) into conduit (11) and partly supplied as fluidizing gas through conduit (12) to the fluidized-bed reactor (6) and partly as cooling gas through conduit (15) to the crystallizer (16). The arrangement of a heat exchanger in conduit (8) is not absolutely necessary, so that the CO(NH$_2$)$_2$ melt can be supplied from the storage tank (2) to the gas scrubber without intermediate cooling.

In the gas scrubber (10) schematically shown in FIG. 2 in a longitudinal section, the upper part includes an orifice plate (38) with a plurality of holes (39), which on the upper surface of the orifice plate (38) each are surrounded by a retaining edge (40) having the shape of the upper portion of a rotation paraboloid and on the bottom surface each are surrounded by an edge (41) having the shape of the counter-portion of the rotation paraboloid. Above the orifice plate (38), the inlet of conduit (27) for the residual synthesis gas and the inlet of conduit (8) for the CO(NH$_2$)$_2$ melt are mounted in the wall of the gas scrubber (10) so as to face each other. In the bottom of the gas scrubber (10), the CO(NH$_2$)$_2$ melt accumulates, is withdrawn therefrom via conduit (42) and recirculated into the process. The cleaned gas mixture containing NH$_3$ and CO$_2$ leaves the gas scrubber (10) via an outlet (43) arranged above the bottom and partly is passed as fluidizing gas through conduit (12) into the fluidized-bed reactor (6) and partly for cooling through conduit (15) into the crystallizer (16).

EMBODIMENT

From the storage tank (2) for the CO(CH$_2$)$_2$ melt, 22 t/h of CO(CH$_2$)$_2$ melt with a temperature of 128° C. are passed through conduit (3) via the pump (4) and conduit (5) into the fluidized-bed reactor (6), wherein NH$_3$ supplied via conduit (7) is fed into the CO(NH$_2$)$_2$ melt flowing in conduit (5). The conversion of the vaporous $CO(NH_2)_2$ to $C_3N_3(NH_2)_3$ is effected in the presence of $Al_2O_3$ at a temperature of 400° C. and a pressure of 3 bar(a). The gas mixture containing $NH_3$ and $CO_2$, which flows in through conduit (11), is partly introduced as fluidizing gas through conduit (12) into the fluidized-bed reactor (6) via the compressor (13) and the heat exchanger (14) used for preheating the gas mixture. The heat required in addition for the catalytic conversion is introduced into the fluidized bed via the heat exchanger (18). The synthesis gas formed in the fluidized-bed reactor (6), which contains sublimed $C_3N_3(NH_2)_3$, $NH_3$, $CO_2$, HNCO, by-products of the catalytic conversion, dust-like catalyst particles and dust-like inert substance particles, leaves the fluidized-bed reactor (6) via conduit (19) and is cooled to a temperature of 255° C. in the heat exchanger (20). In the succeeding gas filter (21), the by-products of the catalytic conversion, which are condensed upon cooling, as well as dust-like catalyst particles and dust-like inert substance particles are removed from the synthesis gas and discharged from the gas filter (21) via conduit (22). Via conduit (23), the synthesis gas flows into the crystallizer (16) and is mixed therein with the gas mixture containing $NH_3$ and $CO_2$, which has a temperature of 125° C., and thereby cooled to a temperature of 200° C., so that $C_3N_3(NH_2)_3$ is resublimed in crystal form. Together with $NH_3$, $CO_2$ and HNCO, the $C_3N_3(NH_2)_3$ crystals are charged via conduit (24) to a gas cyclone (25), in which the $C_3N_3(NH_2)_3$ crystals are separated from the synthesis gas and discharged from the process via conduit (26). The residual synthesis gas containing $NH_3$, $CO_2$, HNCO and possibly traces of sublimed $C_3N_3(NH_2)_3$, which has a temperature of 206° C., is charged to the head of the gas scrubber (10) via conduit (27) and the compressor (28) and washed therein with $CO(NH_2)_2$ melt having a temperature of 128° C., which is supplied via conduit (8) to the head of the gas scrubber (10) at the same level as the residual synthesis gas in an amount of 1460 t/h. Upon separation of the components $NH_3$ and $CO_2$, the $CO(NH_2)_2$ melt accumulating in the bottom of the gas scrubber (10) is introduced into the storage tank (2) and from the same recirculated into the process.

The invention claimed is:

1. A gas scrubber adapted so that a gas stream containing at least one sublimed substance is brought in contact with a liquid or melt stream containing at least one thermally convertible substance, which has a lower temperature than the gas stream, said gas scrubber comprising at least one orifice plate arranged in the upper part of the gas scrubber, said orifice plate comprising a plurality of holes each surrounded by a retaining edge, inlets arranged above the orifice plate for each of the gas stream and the liquid or melt stream, a heat exchanger located in the contact path below the orifice plate, and outlets arranged in the lower part for the cleaned gas stream and the liquid or melt stream.

2. The gas scrubber according to claim 1, wherein the inlet for the gas stream and the inlet for the liquid or melt stream are arranged so as to be directed against each other.

3. The gas stream scrubber according to claim 1, wherein the retaining edge surrounding the holes has the shape of a cone or of the upper portion of a rotation hyperboloid and on the bottom surface of the orifice plate the holes are surrounded by an edge in the form of a counter-cone or a counter-portion of the rotation hyperboloid.

4. The gas stream scrubber according to claim 1, wherein the orifice plate is arranged horizontally within the scrubber.

* * * * *